US008815536B2

(12) United States Patent
Halden

(10) Patent No.: US 8,815,536 B2
(45) Date of Patent: *Aug. 26, 2014

(54) METHODS AND SYSTEMS FOR SAMPLING, SCREENING, AND DIAGNOSIS

(75) Inventor: Rolf U. Halden, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1898 days.

This patent is subject to a terminal disclaimer.

(21) Appl. No.: 10/587,927

(22) PCT Filed: Feb. 4, 2005

(86) PCT No.: PCT/US2005/003369
§ 371 (c)(1),
(2), (4) Date: Aug. 1, 2006

(87) PCT Pub. No.: WO2005/076887
PCT Pub. Date: Aug. 25, 2005

(65) Prior Publication Data
US 2007/0161076 A1  Jul. 12, 2007

Related U.S. Application Data

(60) Provisional application No. 60/541,781, filed on Feb. 4, 2004, provisional application No. 60/577,790, filed on Jun. 8, 2004, provisional application No. 60/619,621, filed on Oct. 18, 2004.

(51) Int. Cl.
| | | |
|---|---|---|
| *C12Q 1/04* | (2006.01) |
| *A62D 3/02* | (2007.01) |
| *C40B 30/10* | (2006.01) |
| *C40B 60/00* | (2006.01) |
| *C40B 60/04* | (2006.01) |
| *C40B 60/06* | (2006.01) |
| *C40B 40/02* | (2006.01) |
| *C40B 60/08* | (2006.01) |
| *C40B 60/10* | (2006.01) |
| *C40B 60/12* | (2006.01) |
| *C40B 60/14* | (2006.01) |

(52) U.S. Cl.
USPC .............. 435/34; 435/262.5; 506/11; 506/14; 506/35; 506/36; 506/37

(58) Field of Classification Search
USPC ............ 435/34, 262.5; 506/11, 14, 35, 36, 37
See application file for complete search history.

(56) References Cited

U.S. PATENT DOCUMENTS

| | | | | |
|---|---|---|---|---|
| 4,784,768 A | * | 11/1988 | Mathieu | 210/321.8 |
| 5,830,596 A | * | 11/1998 | Weiss et al. | 429/93 |
| 5,830,696 A | | 11/1998 | Short | |
| 6,187,530 B1 | | 2/2001 | Scholin et al. | |
| 6,533,914 B1 | * | 3/2003 | Liu | 204/601 |
| 6,730,517 B1 | * | 5/2004 | Koster et al. | 436/47 |
| 7,662,618 B2 | * | 2/2010 | Halden | 435/309.1 |
| 8,323,921 B2 | * | 12/2012 | Halden | 435/30 |
| 2004/0180334 A1 | | 9/2004 | Halden | |

OTHER PUBLICATIONS

Isola et al., 2001. MALDI-TOF Mass spectrometric Method for Detection of Hybridized DNA, Analytical Chemistry, vol. 73, pp. 2126-2131.*
Oman San, 2003. Micro structural characterization of capillary filter produced from a high silica-containing glaze. Materials Letters, vol. 57, pp. 2189-2192.*
Stahl, Soil Science Society of America Journal, 60(3):821-828 (1996).
Isola et al., Analytical Chemistry, 73(9):2126-2131 (2001).

* cited by examiner

*Primary Examiner* — Jon P Weber
*Assistant Examiner* — Kailash C Srivastava
(74) *Attorney, Agent, or Firm* — Edwards Wildman Palmer LLP; Peter F. Corless

(57) ABSTRACT

Apparatus, systems, and methods for detecting, screening and sampling of cells are disclosed.

13 Claims, 5 Drawing Sheets

METHODS AND SYSTEMS FOR SAMPLING, SCREENING, AND DIAGNOSIS

CROSS-REFERENCE TO RELATED APPLICATIONS

This application claims the benefit of U.S. Provisional Application Ser. Nos. 60/541,781, filed Feb. 4, 2004; 60/577,790, filed Jun. 8, 2004; and 60/619,621, filed Oct. 18, 2004. The contents of each of these applications is hereby incorporated herein by reference.

BACKGROUND OF THE INVENTION

Biological monitoring of the growth of cells has applications in fields such as microbiology and medicine. Methods for detecting the growth of microorganisms are well-developed in microbiology laboratories; however, such techniques cannot always be easily applied to real-world situations. For example, isolation and identification of an unknown microorganism can be difficult and time-consuming, particularly when the microorganism is not suited to growth under typical laboratory conditions.

In some cases it is important to study a microorganism in its natural or adopted environment. For example, bioremediation is a recent approach to decontamination of polluted land, water and marine sites, in which microorganisms can be used to remove or destroy contaminants in situ. While bioremediation has been demonstrated to work in some cases, it is often difficult to predict which microorganisms will be most useful at a given site, or which conditions will most effectively promote the bioremediation process. Without considerable information about the types of pollutants and indigenous microbes present at a contaminated site, the selection of appropriate bioremediation conditions is difficult. Unfortunately, due to the relatively inaccessible nature of some contaminated sites (for example, underground water), obtaining such information can be difficult. Conventional sampling and testing can be labor-intensive and time consuming.

The inability to easily and rapidly obtain accurate sampling information also hinders efforts to discover novel microorganisms or natural products, a process often referred to as bioprospecting. Bioprospecting frequently involves searching for organisms in inhospitable or inaccessible environments, such as hot springs, black smokers, deep ocean, and other locales having extreme physical or chemical conditions. However, without adequate means for obtaining complete information about the prevailing conditions and microbial communities in these areas, bioprospecting efforts can be slow and difficult.

While many approaches to these problems have been proposed, few methods have been developed which are rapid, inexpensive, and easily customized for the study of a wide variety of microorganism types and environments.

U.S. Pat. No. 6,187,530 discloses an aquatic autosampler having multiple filters; the device can serially gather samples of microorganisms by exposing one filter at a time to a water sample. However, the device cannot simultaneously collect multiple samples.

PCT Patent Publication WO 2004/081530 discloses an in situ microcosm array (ISMA) technology suitable for environmental monitoring and bioprospecting. The contents of that application are hereby incorporated by reference in their entirety.

Once a sample for study has been obtained, there is a need for rapid and sensitive identification of compounds and microorganisms present in the sample. While many approaches to this problem have been suggested, few methods are capable of detecting species of interest without extensive sample clean-up and purification steps, which can be time-consuming and expensive.

SUMMARY OF THE INVENTION

The present invention provides improved devices, systems, and methods for monitoring environments, e.g., for use in bioremediation, bioprospecting or medical testing and screening. The devices of the invention can be simply made, can be reusable or disposable, and can be used without contaminating the environment being monitored.

The devices can also be made to be compatible with standard automated sample handling systems, thereby permitting automated, high-throughput analysis of samples obtained from the environment under study. Analysis of microorganism-containing samples can be performed using mass spectrometric methods, which can provide rapid, accurate determination of microbial species and/or determine the levels or types of proteins or other cell products produced in a given environment.

The inventive device is useful for monitoring sensitive environments in which contamination is to be avoided. In certain embodiment, the device includes an effluent collection reservoir, for collecting the effluent from the capillary compartments or reagent reservoirs. In this way, release of materials from the interior of the device (fluids, biological organisms or cells, chemical compounds, test compounds, and the like) can be avoided. Thus, in one embodiment, the invention provides an improved, lower cost method for environmental monitoring and bioprospecting.

In another embodiment, the invention provides an improved bioremediation assessment method and tool.

In another embodiment, the invention provides an improved bioremediation assessment method and tool that will enable the automated, large-volume, high-throughput analysis of bioremediation sites.

In another embodiment, the invention provides a monitoring method, tool and analysis strategy that allow for the automated, rapid and simultaneous determination of the following parameters: (1) fluid quality and toxicity, (2) intrinsic bioremediation potential, (3) accelerated bioremediation potential following nutrient amendment, (4) effective bioaugmentation strategies for environmental cleanup, (5) turnover rates of natural compounds and environmental pollutants under natural and enhanced conditions, (6) iii situ DNA synthesis and protein expression, (7) in situ growth/death rates and metabolic activity of native and introduced biological agents under natural and altered environmental conditions, (8) structure and dynamics of microbial communities indigenous to natural environments, and (9) identity and activity of microorganisms of potential value for use in biotechnology.

In another embodiment, the invention provides a monitoring method and tool that may be applied to assess the potential risk resulting from the release of chemicals, potentially hazardous materials, non-indigenous microorganisms, pathogens and genetically engineered microorganisms into natural environments.

In one aspect, the invention provides a method for determining the presence, absence type, or amount of microbes in an environment, without contamination or perturbation of the environment.

In another aspect, the invention provides a method for rapidly determining the optimal growth conditions for a cell in an environment.

In another aspect, the invention provides a method for simultaneously testing a variety of agents to determine the type and amount of an agent capable of inhibiting or stimulating cell growth.

In another aspect, the invention provides a method for screening of various conditions to optimize therapeutic treatments.

In another aspect, the invention provides a method for detecting parasites.

In another aspect, the invention provides a device for measuring the growth of cells in an environment.

In another aspect, the invention provides a device for identifying a cell present in or isolated from an environment.

In another aspect, the invention provides a system for characterizing microorganisms or test compounds present in an environment.

These and other features and embodiments of the invention will be better understood by reference to the description and claims below.

DETAILED DESCRIPTION OF THE INVENTION

Figure 1:
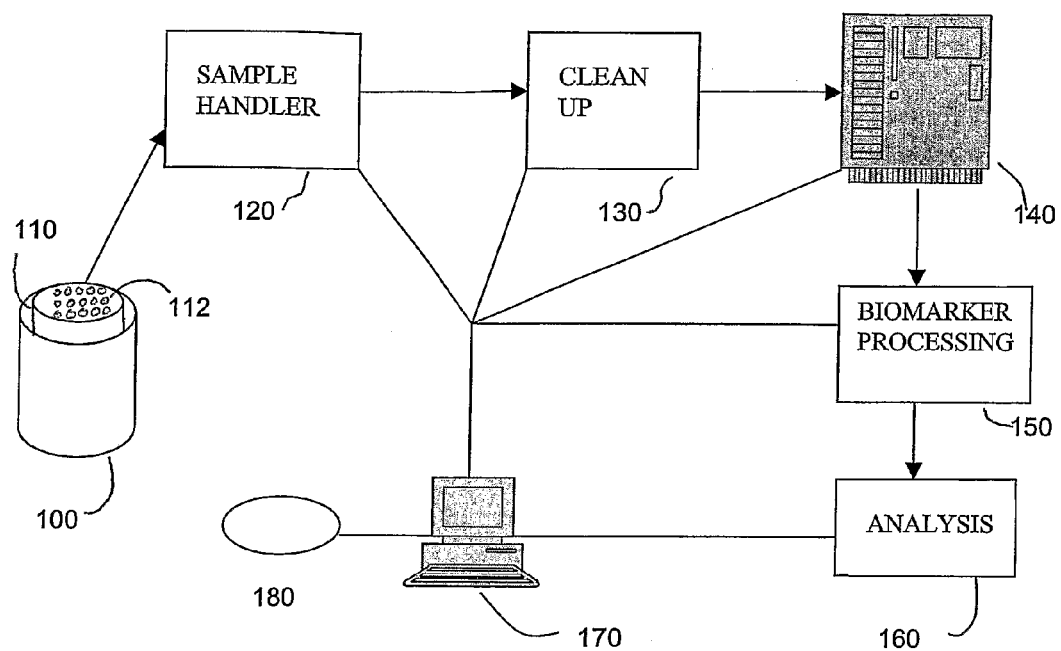
FIG. 1 is a scheme showing one embodiment of a system according to the invention.

The invention provides systems, devices, and methods for monitoring test environments, including biological fluids, preferably without contamination of the test environment.

In one aspect, the invention provides a device for sampling or studying a test (e.g., environmental) fluid. The device includes a) a housing having at least one opening in a wall thereof; b) an array assembly disposed within the housing and comprising a plurality of capillary microcosms, each capillary microcosm having a fluid inlet, a fluid outlet, and a capillary chamber; c) a fluid manifold in fluid communication with the opening in the housing and the plurality of capillary microcosms; and optionally d) an effluent reservoir for collecting effluent from the fluid outlets of the capillary microcosms.

In preferred embodiments, the device includes at least one effluent reservoir or container in fluid communication with a fluid outlet of at least one capillary compartment or chamber, for collecting and retaining the effluent from the chamber(s). The effluent reservoir or container may take the form of a rigid container, a flexible bladder, or a bibulous or absorbent material for absorbing fluid. The effluent reservoir can be situated within the device housing, or it can be secured through a fluid-tight seal to a fluid outlet of the device housing. The effluent reservoir or container preferably is located within the device housing. By retaining the effluent within the housing, the possibility of fluid leakage (and resultant contamination of the external environment) can be minimized.

By collecting the effluent from the capillary compartments, materials from the interior of the device (biological organisms or cells, chemical compounds, test compounds, and the like) are not released into the environment external to the device. Thus, the devices and methods of the invention are well-suited for use in sensitive environments which should not be perturbed.

Examples of sensitive environments include: in vivo uses, where the device is implanted into a human or animal body; surface or subsurface water sources, including surface reservoirs and sub-surface aquifers or water tables; food supplies; sterile environments (such as laboratories or hospital operating theaters); clean rooms for manufacturing; environments in which introduced organisms could be harmful (including, e.g., probes for use in outer space and planetary exploration); and the like. In certain applications, a sensitive environment can be tested by placing the device of the invention outside an environment of interest but is in fluid communication with the environment. For example, fluids can be piped or flowed from an environment of interest to the device of the invention for testing.

In a preferred embodiment, the test environment contains a fluid, such as water, an aqueous solution, or an aqueous bodily fluid (such as blood, serum, plasma, saliva, urine, cerebrospinal fluid, or the like), in which the device of the invention is immersed. In another embodiment, the test fluid is a gas, e.g., an atmospheric gas such as air.

In a preferred embodiment, there is a separate effluent reservoir associated with each capillary chamber or microcosm within the array. By collecting effluent from each chamber individually, the effluent of each microcosm can be saved for later analysis when the device is removed from the test environment, permitting data to be obtained for each individual microcosm.

In another embodiment, the invention provides a method for optimizing medical treatment for a patient either in vivo or ex vivo (e.g., in vitro). The method includes the following steps: a) providing a device comprising a housing and an array of capillary microcosms, each of the capillary microcosms being in fluid communication with a fluid manifold, and each of the capillary chambers containing either i) a first sample type associated with a disease state of the patient, ii) a second sample type not associated with the disease condition, or iii) both a first sample type and a second sample type; b) subjecting each of said samples to a treatment condition; c) determining the effect of the treatment condition on each sample; and d) selecting an optimized medical treatment for the patient. It will be appreciated that the first and second sample types can be, e.g., samples of diseased and normal tissues, respectively; samples of potential donor and recipient tissue, e.g., for evaluating the feasibility of transplants, and the like.

In another embodiment, the invention provides a method for optimizing medical treatment for a target population (e.g., a particular species, or a subpopulation of a larger population). The method includes the following steps: a) providing a device comprising a housing and an array of capillary microcosms, each of the capillary microcosms being in fluid communication with a fluid manifold, and each of the capillary chambers containing either i) a case sample associated with a disease state occurring in the target population, ii) a control sample or iii) both a case sample and a control sample; b) subjecting each of said case and control samples to a treatment condition; c) determining the effect of the treatment condition on each sample; and d) selecting an optimized medical treatment for the patient. In this embodiment, the control sample can be, e.g., a sample from a member of the larger population who is unaffected by a particular condition.

The Housing

The material for the exterior of the housing is preferably selected for use in the test environment. For example, the housing can be rigid for use in demanding applications, or flexible, e.g., for use where the device is to be worn on or even in (e.g., implanted in) a living body. To avoid contamination, in certain embodiments the exterior of the housing can be washed, decontaminated, disinfected, and/or sterilized, e.g., by heating, by irradiation, use of chemical sterilants such as alcohol, and the like. A suitable material will be selected to be compatible with such conditions. The material for the housing can also be selected to resist extremes of temperature, pressure, pH, corrosion, or other adverse conditions that may be present at the selected test site, either by using an appropriate body wall material or by coating a body wall material with an appropriate surface chemistry.

In certain preferred embodiments, the housing is constructed of materials such as steel, aluminum, or plastic, although other materials can be selected. Titanium or other biocompatible materials can be used for devices intended for in vivo use.

The housing will generally be selected to be of a size and shape adapted for the intended use of the device, e.g., sized to fit within a borehole of a well, or miniaturized for implantation into a living body. In addition to containing the capillary array, the housing may contain other components, such as the fluid manifold, a battery or other power source (e.g., a fuel cell), an effluent reservoir, pumps, valves, reagent reservoirs, sensors, signal transduction equipment, and the like.

In certain preferred embodiments, microprocessor control circuitry, e.g., for the control of valves, pumping devices, controls, sensors and other electronic controls, or for acquisition of data from such devices, are integrated into the device to form an integrated unit (e.g., see below).

The Capillary Array

The capillary array includes a plurality of test chambers, or microcosms, each adapted for containing a cell sample (e.g., microorganisms or tissue samples) or a sample of a test compound. Each chamber has a fluid inlet and a fluid outlet; both the inlet and the outlet can be controlled with valves to control the flow of fluid into and out from each chamber. Such controls can be configured to permit control of fluid flow through the chambers individually, or to permit operation of certain chambers simultaneously. A check valve can be provided at the outlet of each chamber to prevent backflow of fluid into the chamber.

In one embodiment, the capillary array contains a standardized number of capillary chambers (e.g., 96, 384, 1536) corresponding in size and configuration to standard microtiter plates. By using a standard size and footprint for the capillary array, it is possible to use standardized robotic handling equipment (e.g., liquid handlers) to load, unload, or analyze the contents of the chambers. In one embodiment, the capillary array comprises a block of polytetrafluoroethylene (Teflon) resin. Customized microtiter formats include plates having a plurality of capillary chambers (e.g., 48, 100, or 100,000 capillary chambers.

The capillary chambers or compartments (microcosms) of the device can be provided with a variety of materials for adjusting or perturbing the conditions within the chamber. For example, a chamber may optionally include a substrate (such as a filter or other material, e.g., glass wool) suitable for collecting bacteria from a fluid flowing through the chamber. Filter materials can be selected from many commercially-available sources, for example, nitrocellulose filters, nylon membrane filters, and the like. In certain embodiments, a filter material is compatible with both the collection of microorganisms (or other cells) and subsequent culture of the microorganisms. In addition to filtration, microorganisms, compounds or particles can be collected in the microcosms by sorption, precipitation, sedimentation, coagulation, extraction, chromatography, affinity separation, size exclusion separation, passive attachment to presented surfaces, or active attachment to presented surfaces.

The capillary array can be used for capturing, isolating, growing, or testing a variety of cell types, including bacteria, fungi (including yeasts), parasites, protozoa, and cells or tissue samples (such as biopsies) isolated or obtained from multi-cellular organisms (e.g., tissue culture of plant cells, animal cells, insect cells, mammalian cells, and the like). The chambers can also be used for the study of viruses, prions, and other infectious particles. Thus, the systems and methods of the invention can be used to study viruses, prokaryotes including, but not limited to, bacteria, and Archaea, and eukaryotes including, but not limited to, yeasts, fungi, protozoa, plant cells, animal cells, and mammalian cells. The term "microorganism," as used herein, is intended to include bacteria, fungi, parasites, protozoa, and viruses, and further includes spores, seeds, and other vegetative forms of microorganisms. The term "cell", as used herein, is intended to encompass living cells, whether of single-celled or multi-cellular organisms, and also include spores, seeds, larvae, and other forms.

A chamber can include a growth medium or food source for growth of cell or tissue cultures. In certain preferred embodiments, the food source can be specific to a particular cell type (such as a specific microorganism) which is to be studied. For example, as described elsewhere herein, *Sphingomonas wittichii* Strain RW1 is a bacterium capable of degrading dioxins and dibenzofurans. Few other bacteria are capable of using dibenzofuran as a food source; thus, a test chamber containing dibenzofuran can be used to selectively culture *S. wittichii* Strain RW1. As described elsewhere herein, such a food source can be isotopically labeled to provide additional information about any cells capable of growth, metabolism, reproduction, and production of biomolecules and parasites (e.g., viruses) in the presence of the food source. As an alternative, a chamber can be loaded with one or more microorganisms that were grown on isotopically labeled food sources and whose growth, metabolism, reproduction, and production of biomolecules and parasites (e.g., viruses) can be tested by determining the loss of isotopes or redistribution of isotopes over time.

A chamber can also include test compounds for determining whether a cell can grow in the presence of the test compound, e.g., the test compound can be an antibiotic, an antineoplastic agent, and the like. These compounds can be provided in a matrix or formulation that allows gradual release of the compound into the chamber.

The chambers can also be provided with means for containing cells, reagents, or other materials within the chamber. For example, a membrane can be used to retain cells or certain compounds while allowing other materials to pass through the chamber and into an effluent collection reservoir.

It will be appreciated by the skilled artisan in light of the present disclosure that the devices and methods of the invention can be used to test for many properties of substances other than cells. For example, the chambers of the device can be loaded with candidate pharmaceuticals (e.g., to test for desirable activities, as well as undesirable side effects); with candidate biocompatible materials (e.g., to test for low immunogenicity, resistance to biofilm formation, anti-coagulant properties, resistance to corrosion, and the like); or with potential toxins (e.g., environmental contaminants, biowarfare agents, compounds for use in commercial products, e.g., preservatives, plasticizers, and the like). Such materials can be tested to determine the suitability of a material for use in an environment (e.g., to determine durability or wear qualities such as resistance to corrosion, dissolution, erosion, hydrolysis, or the like) or to determine the effect the compound has on the environment (e.g., toxicity, changes to pH, corrosiveness, and the like).

In addition, reagents can be carried in a reagent reservoir, e.g., a reservoir within the device housing, which is in fluid communication with the fluid manifold, or directly with a chamber or chambers of the array. Valves and a pump or pumps control release of a reagent or reagents from the reagent reservoir to a capillary chamber or chambers as needed. Examples of such reagents include compounds undergoing testing (e.g., as described above), or materials for use the experimental conditions established in a chamber (e.g., growth media, preservatives, fixatives, dyes, nucleic acid hybridization probes, antibodies, cytotoxic agents, antibiotics, salts, enzymes for cell manipulation (e.g., trypsin for cell digestion) and the like.

Microscale Devices

Especially when in vivo monitoring is desired, miniaturization of the device is advantageous. Thus, in certain embodiments, the device is a micro-electromechanical system (MEMS). MEMS technology generally involves fabrication of microscale devices from silicon wafers (see, e.g., M. J. Madou, Fundamentals of Microfabrication: The Science of Miniaturization, $2^{nd}$ ed. (CRC Press, 2002)). For example, in one embodiment, a capillary chamber is etched into a silicon substrate; microchannel fluid pathways, valves, and pumping devices for pumping fluid to the capillary chambers are similarly made on the silicon substrate. The device can also incorporate miniature flow sensors. In this embodiment, each fluid flow into each capillary chamber can be controlled individually and precisely, thereby enhancing the capabilities of these devices. The flow sensors also allow detection of blockage or other abnormal flow conditions within the device.

In preferred embodiments, microprocessor control circuitry for the valves, pumping devices, controls, sensors, and other electronic components of the device are integrated into the MEMS substrate chip to form an integrated device.

Only a very small amount of power is required to operate a MEMS device; the power can be supplied from an on-board battery or via radiofrequency (RF) power supplied by an external RF power source. RF technology is well suited to implanted devices, which can then be powered, operated, and monitored remotely.

A microscale device can be constructed as described in U.S. Pat. No. 6,653,124, the contents of which are incorporated herein by reference in their entirety. For example, a substrate layer can be etched or micro-machined with an array of microchambers for containing biological cells or chemical compounds to be detected or tested, fluid channels for communication with the chambers, and microfluidic devices such as valves and pumps for directing fluid flow to the chambers.

If biological cells or test compounds are to be provided within the microchambers prior to emplacement of the device in a test environment, such test materials can be printed or dispensed into the microchambers using automated slide spotters or microprinters capable of delivering micro- or nanoliter-scale spots or droplets of the materials to be included in the microchambers.

The substrate layer is then adhered or attached to a covering layer, optionally with a spacer (optionally a membrane for sealing and isolating the microchambers) to provide separation between the two layers, to provide a miniaturized device according to the invention.

The entire device can be encapsulated within a layer or envelope of a suitable biocompatible material, making provision for an opening for access of the external fluid to be tested to the interior of the device. The opening can be or may contain a selective barrier, e.g., a membrane to prevent entry into the device of large particles which could foul or clog the device.

Sensors

A device of the invention optionally include one or more sensors for measuring a state or property of the cells or fluids within the device. For example, a sensor can be located in (or downstream from) a chamber containing cells, so that fluid passing over or through the cells is directed to the sensor for measurement of a property of interest. See, e.g., U.S. Pat. No. 6,806,543 for an example of a microfluidic apparatus comprising a sensor.

By incorporation of sensors into the device, it is possible to monitor the conditions in the environment in real time. Such monitoring is useful for determining, e.g., when a pre-selected end-point for an experiment is reached (e.g., when a collection reservoir or effluent container is full, when all of an added compound has been consumed by microbial growth, when all cells have been killed by a treatment), so that the device can be removed from the environment and analyzed, reused, or discarded.

Examples of sensors include electrochemical sensors, such as oxygen sensors, e.g., for measuring biological oxygen demand (BOD) (see, e.g., U.S. Pat. No. 6,689,602 for a compact oxygen sensor suitable for measuring BOD) and glucose sensors, for measuring glucose concentration of a fluid, e.g., blood or urine (see, e.g., U.S. Pat. Nos. 6,815,186, 6,721,587 and 6,673,596); temperature sensors; pressure sensors; optical sensors, e.g., for performing fluorescence assays of cells within the chambers in real-time; and the like.

A sensor can be wired to transmit information to a control or data-handling element, such as a microprocessor, which may be an integral part of the ISMA device or may be external to the device (e.g., a remote control unit). Wires or leads for communication of a sensor with a control or data-handling element can be provided according to well-known principles.

Operation of the Device

In operation, the device is first readied by addition of any biological cells or materials, or chemical reagents needed, as described above. The device is then placed into the test environment, which, as described herein, can be a well, a living body, a catheter line or other fluid conduit, or any other environment in which in situ testing is desired. The device can be placed into the test environment remotely, e.g., using a robotic arm or other mechanical device. To prevent contamination of the test environment, the device can be disinfected, washed, or sterilized prior to placement in the environment.

The device can be operatively connected to a control unit for operation of the device. Such a connection can be a wired connection, permitting signals from the control unit and data from the device to be exchanged, or the device and control unit can be equipped with transceivers for receiving control signals and transmitting data by radio telemetry.

Figure 2:
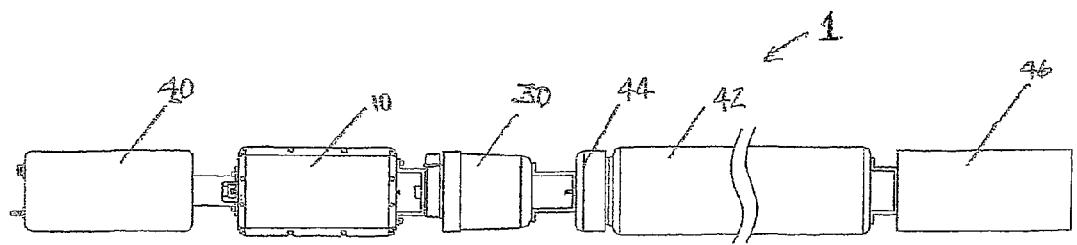
FIG. 2 is a schematic representation of a preferred embodiment of a device according to the present invention.
Figure 3:
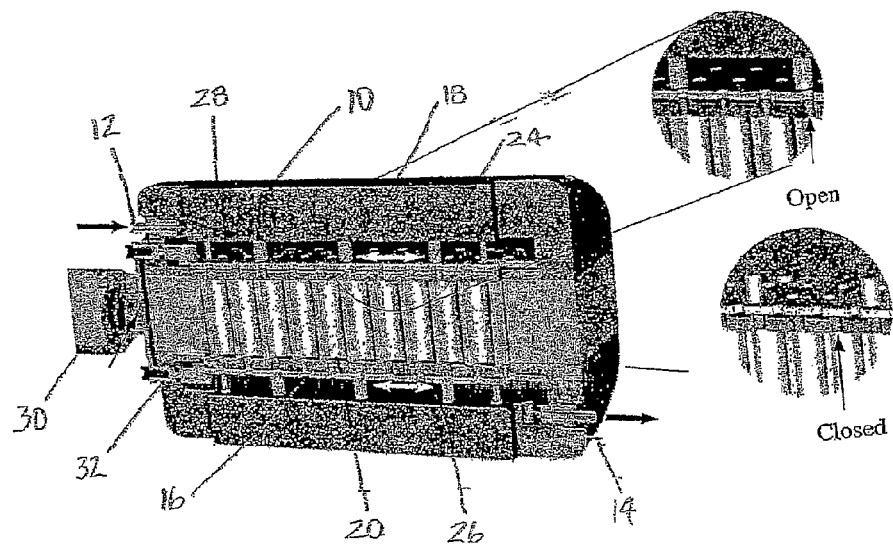
FIG. 3 is a cross-sectional view of the housing shown in FIG. 1, with enlarged representations of a valve plate adjacent to capillary inlets in both their open and closed positions.
Figure 4:
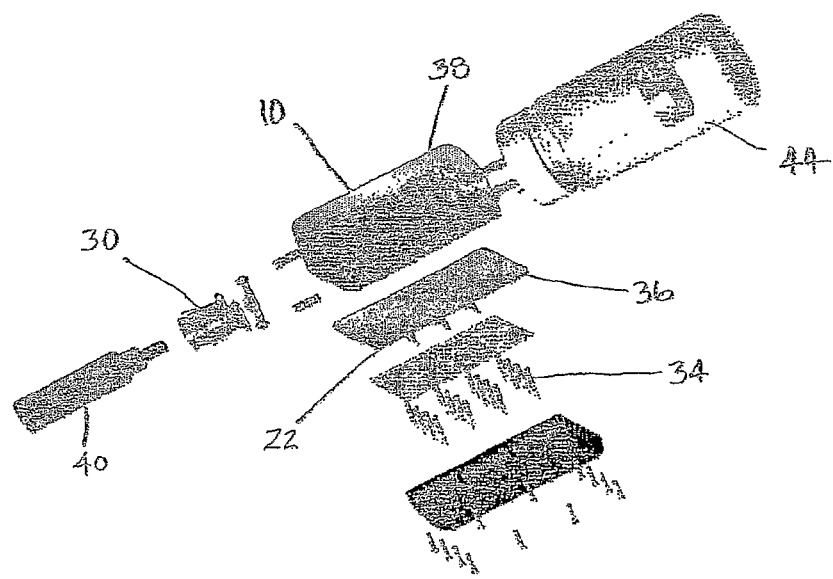
FIG. 4 is an exploded view showing a valve plate of FIG. 1 and the components that are used to cause it to move laterally to open and close the capillary's inlet.
Figure 5:
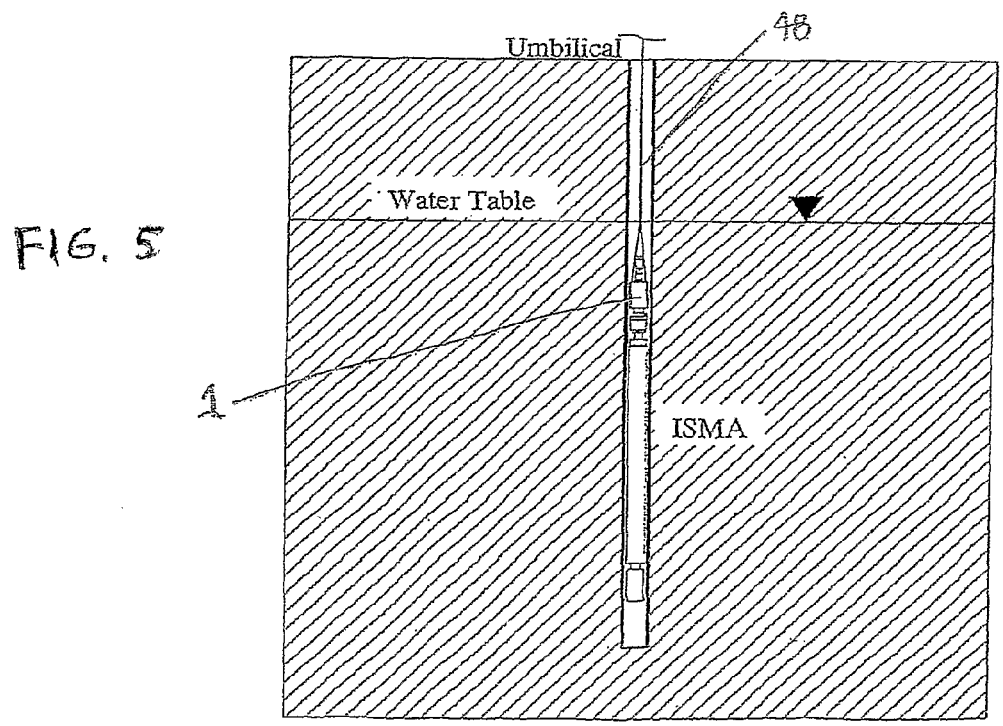
FIG. 5 is a schematic representation of a preferred embodiment of the present invention being extended down a groundwater monitoring well.

When the device has been placed in the test environment, a valve (or other device adapted for starting, stopping and/or metering fluid flow) is opened, admitting fluid to the interior of the device and into the fluid manifold. Fluid is admitted into the individual chambers by controlled opening and closing of valves (see, e.g. FIG. 2). By exposing various chambers to the fluid over a period of time, changes in the fluid composition over time can be observed.

When the device has been placed, real-time data can be obtained from sensors as described above, to monitor the progression of the experiment. The sensors can provide information such as, e.g., whether the device is functioning properly, when a chamber is full or empty, whether cells are growing (e.g., by monitoring BOD), and the like.

The monitoring or testing process can be allowed to proceed for a pre-determined time and then terminated, or else real-time data can be used to determine when the experiment should be ended. For example, an experiment can be ended when all chambers of the microcosm array have been filled with fluid, when all reagents contained in a reagent reservoir have been consumed, when sensor measurements indicate that no further bacterial metabolism is occurring, or the like.

When the monitoring or testing process is complete, the device is removed from the test environment, e.g., by retrieving the device via an umbilical or removing the device from a test fluid sample.

Once the device is removed from the test environment, the identity of any microbes or cells present in the capillary chambers can be determined by a variety of methods, some of which are known in the art. Such methods include genomic, proteomic, physical, chemical, and biochemical approaches.

Detection and Identification of Microbes and/or Cells

In one embodiment, the invention provides a method for detecting and/or identifying cells (e.g., microorganisms) having a pre-determined phenotype. The method comprises the steps of providing a sample for testing; and detecting by mass spectroscopy the presence or absence of a biomarker diagnostic of, e.g., a microorganism having the pre-determined phenotype in the sample. A biomarker can be selected prior to beginning the analysis. The sample can be, e.g., a sample from a device of the invention, e.g., a sample from a capillary microcosm. The presence or amount of the biomarker in the sample can then be correlated with the presence of the microorganism having the pre-determined phenotype.

As used herein, the term "biomarker" refers to any detectable biological (e.g., metabolic) product useful as a marker or signal for the presence of a cell, e.g., a microorganism. A "pre-determined phenotype" refers to a phenotype for which a biomarker is known or can be determined. A biomarker is diagnostic for, or indicative of, a pre-determined microorganismal phenotype when detection of the biomarker provides a reliable indication that a microorganism having the pre-determined phenotype is present in a sample being tested.

The selection of a suitable biomarker will be routine for one of skill in the art. Preferably, a biomarker will be unique to a pre-selected phenotype; that is, the biomarker will be specific to the species and phenotype of interest. The biomarker should also be capable of detection by an analytical system such as a mass spectrometer; for certain embodiments, it is necessary that a biomarker be ionized or ionizable for mass spectrometric analysis. In preferred embodiments, a biomarker is a peptide or protein, and the sequence of the peptide or protein is known; preferably, the sequence is stored in a computer database for use in analytical determination of the biomarker, e.g., by MS.

In contrast to conventional methods of bacterial detection, the methods of this invention can provide information not only about the presence or absence of a particular cell type (e.g., bacterial type) or species (e.g., the genotype of a bacterium), but also about the expressed phenotype of the cell (e.g., the types and amounts of gene products produced by the cell, e.g., bacterium). In some cases, the phenotype of the microorganism depends upon the environment in which the organism is grown. For example, as described in further detail herein, certain bacteria express dioxin dioxygenase only when grown in the presence of a suitable substrate for the enzyme. The presence of this enzyme in a sample therefore demonstrates not only the presence of the particular species of bacterium, but also that the bacterium is capable of producing the dioxygenase, and that a suitable substrate for the enzyme is present in the bacterial environment. As is described in more detail elsewhere herein, an enzyme or other protein can be detected by detection of the whole enzyme or by fragments of the enzyme. Thus, a portion of a characteristic enzyme can serve as a biomarker for the presence of the organism of interest.

Thus, the invention provides methods for determining whether a cell (e.g., a bacterium) having a selected property (e.g., a cell capable of performing a pre-selected function) is present in a sample or environment. For example, the invention provides methods for determining whether a bacterium capable of biodegrading a substrate is present in a sample (e.g., by detecting a biomarker diagnostic for such biodegradation activity). As another example, the methods of the invention can be used to study in near-real time the level of functional enzymes in biotechnology production fermenters and reactors, permitting quality control of processes and products.

As an example, monooxygenase and dioxygenase enzymes are frequently associated with microorganisms (e.g., bacteria or fungi) useful in bioremediation, because such enzymes are capable of degrading a variety of substrates. In certain embodiments, the bioremediation application is removal or degradation of aromatic hydrocarbons (e.g., dioxins, toluene, xylene, naphthalene biphenyl, styrene, 2,4,6-trichlorophenol, and the like). In certain embodiments, the bioremediation application is removal or degradation of nitroalkanes or nitroaromatic compounds (e.g., 2-nitropropane or 2-nitrotoluene), which may be the result of industrial production of pesticides, explosives, dyes, pharmaceuticals and plastics. In certain embodiments, a method of the invention comprises detecting the presence or absence of a monooxygenase or dioxygenase enzyme in a sample, with the presence of the enzyme being associated with the presence of a bacterial phenotype useful for bioremediation. In certain embodiments, the enzyme is an oxygenase, such as toluene-o-monooxygenase, methane monooxygenase, styrene monooxygenase, xylene monooxygenase, squalene monoxygenase, cyclohexanone monooxygenase, butane monoxygenase, 2,4,6-trichlorophenol 4-monooxygenase, and the like. In certain preferred embodiments, the enzyme is a dioxygenase such as dioxin dioxygenase, naphthalene dioxygenase, biphenyl dioxygenase, phenanthrene dioxygenase, toluene dioxygenase, 2-nitrotoluene dioxygenase, 2,3-dihydroxybiphenyl 1,2-dioxygenase, catechol 1,2-dioxygenase, protocatechuate-3,4-dioxygenase, 2-nitropropane dioxygenase and the like. In a preferred embodiment, the enzyme is dioxin dioxygenase and the microorganism is *Sphingomonas wittichii* Strain RW1. In another embodiment, the enzyme is the dioxygenase gi|37727200 of *Pseudomonas putida* KT2440.

In certain preferred embodiments, biomarker activity or level in a microorganism of interest (e.g., microorganisms having a pre-determined phenotype, bacterium capable of performing a pre-selected function) in a sample is induced or upregulated in the microorganism prior to analysis of the sample to detect the biomarker. By inducing higher levels of expression of the biomarker, detection of the biomarker (and therefore the microorganism) is improved. Induction of enzymes can be achieved according to known methods. For example, as described herein, the amount of dioxin dioxygenase produced by *S. wittichii* Strain RW1 can be modulated (i.e., increased or decreased) by selection of appropriate growth media. Similarly, production of toluene dioxygenase by *Pseudomonas putida* Strain TVA8 can be increased by addition of an appropriate concentration of toluene in the growth medium. By increasing production, expression, or levels of a biomarker in a sample, detection of the biomarker is simplified, and the need for sample clean-up, preparation or other manipulation prior to analysis can be reduced. As described elsewhere herein, a device of the invention, comprising an array of microcosms suitable for growth or culture of microorganisms, can be used to investigate the effects of a variety of growth conditions on the production, expression, or level of a biomarker in a sample.

In certain embodiments, samples are subjected to minimal processing or clean-up steps prior to analysis. For example, MS techniques are capable of detecting biomarkers in digests of whole cells (see, e.g., Examples 2-5 herein and FIG. 6). By analyzing pre-determined biomarkers that are relevant for an activity of interest (e.g., bioremediation), only microorganisms relevant to the activity will be detected if present; the presence of other organisms which do not have the desired phenotype may not interfere with the analysis. Moreover, as described above, by selecting conditions (e.g., carbon source, temperature, and the like) which favor the expression of relevant biomarkers, greater robustness of detection can be achieved, and the need for sample clean-up can be reduced.

The invention also provides methods for determining whether a microorganism capable of infecting a subject (including a human) is present in a sample, e.g., by detecting a protein characteristic of an infective state of such a microorganism (such as a parasite). In certain embodiments, a method of the invention comprises detecting the presence or absence of a protein associated with an infectious form or stage of a microorganism, including a parasite.

Figure 6:
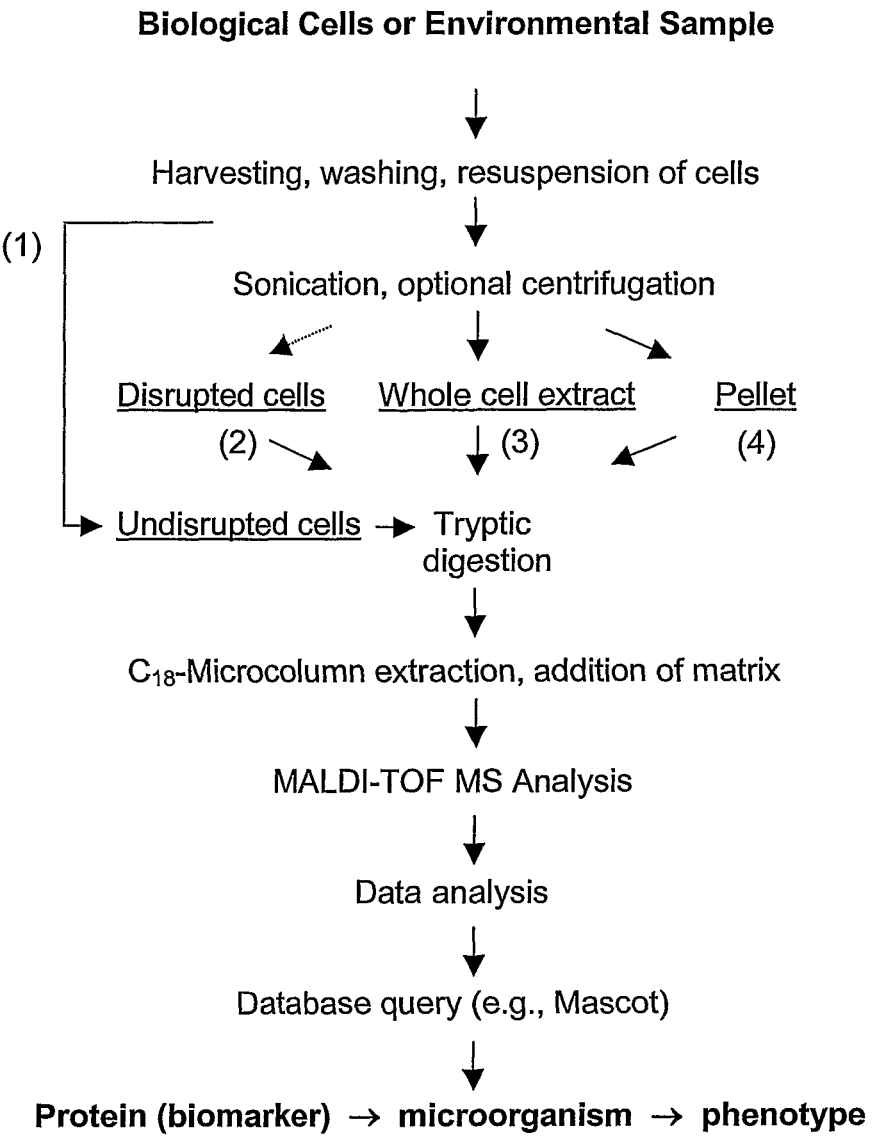
FIG. 6 is a scheme showing a method for identifying biological cells, including microorganisms such as bacteria.

One analysis scheme according to the invention is shown in FIG. 6. As shown in FIG. 6, a bacterial sample (such as a culture, e.g., a culture obtained from a device of the invention) is harvested or sampled, and whole cells or sonicated fractions of cells are subjected to enzymatic digestion with trypsin. Following digestion, optional sample clean-up with a microcolumn is followed by preparation of the sample for mass spectrometric analysis; shown is the preparation of a matrix for MALDI MS. The data obtained from the MS analysis is then analyzed and compared to a database for identification of peptides or peptide fragments present in the sample, which indicate the presence of a characteristic enzyme present in the sample. By detecting an enzyme associated with a particular phenotype of the microorganism, the presence of a bacterial phenotype having a particular function can be detected.

A preferred method of identifying organisms (or biomarkers associated with organisms) is mass spectrometry (MS). Certain mass spectrometric techniques are highly sensitive and are capable of detecting small quantities of analyte, even in the presence of other potential interfering materials. One particularly preferred MS is matrix-assisted laser desorption/ionization time-of-flight mass spectrometry (MALDI TOF MS). MS has been used to identify organisms using intact cells or spores (see, e.g., Krishnamurthy and Ross, *Rapid Commun. Mass Spectrom.* 10:1992-1996 (1996); Leenders, F. et al. *Rapid Commun. Mass Spectrom.* 13:943-949 (1999)). MS analysis of cellular constituents such as proteins, nucleic acids, and lipids has also been reported (see, e.g., Demirev, P. A. et al., *Anal. Chem.* 71:2732-2738 (1999)). The use of protein database searching has increased the speed and versatility of the analysis when proteins are used to identify the organism (see, e.g., Perkins, D. N. et al., *Electrophoresis* 20:3551-67 (1999)). For example, the NCBI and Mascot databases contain theoretical peak data that can be used to identify proteins. Data from mass spectrometric analysis can be manipulated and analyzed using commercially-available software such as Data Explorer (Applied Biosystems).

Protein sequencing of enzymatic digests using multidimensional MS techniques (MS$^n$) including tandem mass spectrometry (MS/MS)) can also be used to identify organisms or expressed gene products in the microcosm of the invention. Such proteomic approaches permit rapid, highly automated analysis (see, e.g., K. Gevaert and J. Vandekerckhove, *Electrophoresis* 21:1145-1154 (2000)).

The identification of microorganisms by MS can advantageously be performed by isolation of the microorganism, followed by MS analysis of either the whole cell, or proteins, such as the ribosomal proteins. Robotic devices can be integrated with MS instruments to provide for automation of this analysis technique. For example, commercially available robotics allow for fully automated sample preparation and analysis, including sample clean-up and concentration, preparation and imaging of two-dimensional (2D) electrophoresis gels, harvesting and enzymatic digestion of the protein spots, and preparation of the enzymatic digests for MS analysis. One commercially-available system for high-throughput in-gel digestion, sample cleanup, and MALDI spotting is the MultiPROBE II Proteomics Workstation from PerkinElmer, Inc. An alternative to gel electrophoresis for protein isolation is liquid chromatography (LC); LC-MS (including LC-MALDI TOF) interfaces have been reported (see, e.g., U.S. Pat. No. 6,140,639).

However, MS analysis can be complicated when more than one microbial species is present. One way of simplifying the analysis is by use of isotopically-labeled substrates for microbial growth. Thus, if $^{13}$C-labeled carbon sources are provided, an organism capable of metabolizing that carbon source will incorporate $^{13}$C if the organism grows under the ambient conditions in the ISMA. MS detection and isotopic comparison with reference materials can reveal which biomarkers have incorporated $^{13}$C; in the case of mixed cultures of microorganisms, these biomarkers can also be identified to determine which microorganisms were capable of growth using the isotopically-labeled compound as a carbon source in situ. Similarly, isotopically labeled microorganisms can be tested in the ISMA to determine their behavior in an environment of interest and to study the flow of energy in a complex system via tracing of the isotopes.

The present inventor has found that identification of certain proteins characteristic of a specific organism can be achieved by mass spectrometric (e.g., MALDI TOF MS) analysis of cell lysates. For example, *Sphingomonas wittichii* Strain RW1 is a bacterium capable of mineralizing dioxin and related compounds (see, e.g., Halden, R. U, "Engineered in situ biodegradation of dioxins and related compounds" Ph.D. Thesis. University of Minnesota, Minneapolis, Minn. (1997)). The biotransformation activity of this organism is due, at least in part, to the presence and concentration of dioxin dioxygenase, an enzyme which initiates degradation of dioxins and dibenzofuran. The presence of *S. wittichii* in culture can be determined by MALDI TOF detection of dioxin dioxygenase in tryptic digests of RW1 cells. While detection of dioxin dioxygenase in whole cells appeared possible, better results were obtained through sonication of whole cells, preferably followed by centrifugation of the whole cell extract and analysis of the supernatant (see, e.g., FIG. 6 for a description of the analysis). Under these conditions, the presence of the alpha subunit of dioxin dioxygenase, and therefore the presence of *S. wittichii* in culture, can be determined when at least $10^6$-$10^7$ cells (grown in the presence of dibenzofuran) were analyzed by MALDI TOF MS with protein database searching.

Parasites can also be detected in an analogous fashion. Thus, for example, *Schistosoma mansoni*, a parasite transmitted through water, was detected by isolation of parasitic cercariae (larval stage), sonication of whole cercariae, centrifugation, trypsin digestion of the supernatant (containing soluble proteins), and MALDI TOF MS analysis. Comparison of MS-detected peptide fragments to the NCBI metazoan database yielded a best match to a stathmin-like protein of *S. mansoni* using peptide mass fingerprinting in conjunction with one-dimensional MS. This method is rapid and specific for the detected parasite, and provides information regarding the presence or absence of infectious forms of the parasite, by detecting the stathmin-like protein that is expressed only in infectious lifecycle stages of the parasite. This method provides a rapid method for sampling and testing water sources to determine whether infectious schistosomal parasites are present. In addition, the devices of the invention can be used in situ to explore conditions suitable for eradication of such parasites. The confidence of identification of such detections can be raised by further analyzing detected characteristic masses using multi-dimensional MS.

In addition to, or as an alternative to, MALDI TOF MS analysis, multidimensional mass spectrometric analysis (e.g., MS/MS) can be used to identify proteins. If the number of target peptides is insufficient for successful detection by peptide mass fingerprinting (PMF), fragmentation of detected biomarkers and MS/MS of the resultant peptide fragments can be used to sequence the peptides and proteins of interest according to well-known methods. Peptide sequencing by MS/MS and MS$^n$ can be used alone, or as a confirmation of a protein identified by database matching in a MALDI TOF analysis. Similarly, undigested target biomarkers can be detected by MALDI TOF MS in linear mode and their identity confirmed by MS/MS analysis of fragments produced during tandem mass spectrometry according to well-known methods.

Another useful technique for identifying microorganisms is the use of arrays of nucleic acid probes on a "chip" (see, e.g., A. Troesch et al., *J. Clin. Microbiology* (1999) 37(1): 49-55). In this method, nucleic acids from a microorganism are isolated, amplified if necessary (e.g., by polymerase chain reaction (PCR)), and selective binding to an array of nucleic acid probes is used to identify the microorganism. The isolation and amplification steps are preferably performed in an automated fashion using commercially-available robotic equipment.

Other methods for identification of cells, proteins, or other compounds of interest can be used. For example, cells (including bacteria), viral particles, or antigenic proteins can be identified by standard immunoassays, using an antibody to the material of interest. The antibody can be labeled in any conventional fashion, and binding of the antibody (indicating the presence of the target) can be detected by a variety of methods (detection of radioisotopes in radioimmunoassay, colorimetric detection for enzyme-linked immunosorbent assay (ELISA), chemiluminescent detection, and the like). Other protein identification methods include 1- and 2-dimensional electrophoresis, immunoblotting, affinity chromatography, and other standard techniques.

Systems

In another aspect, the invention provides a system for characterizing microorganisms present in an environment. The system includes a) a collection device having a plurality of capillary microcosms for collecting microorganisms or test compounds; b) a sampling device for sampling or manipulating microorganisms present in the capillary microcosms; and optionally c) an analysis device, such as a mass spectrometer, for characterizing the microorganisms in the capillary microcosms; wherein the sampling device is adapted to provide a plurality of samples to an analysis device.

The collection device of the system is a device as described hereinabove having an array of capillary microcosms. As described above, in preferred embodiments the capillary array contains a standardized number of capillary chambers (e.g., 96, 384, 1536) corresponding in size and configuration to standard microtiter plates. By using a standard size and footprint for the capillary array, it is possible to use standardized robotic handling equipment (e.g., liquid handlers) to load, unload, or analyze the contents of the chambers.

The system includes a sampling device for sampling microorganisms or test compounds present in the capillary arrays, e.g., after removal of the collection device from the test environment. The sampling device is preferably an automated sample handler, such as an automated liquid handler or other sampling handling station. Commercial liquid handlers compatible with standard 96-well microtiter plates are readily available.

The system also includes an analysis device such as a mass spectrometer for characterizing the microorganisms or test compounds present in the capillary microcosms. Certain mass spectrometric methods for characterizing microorganisms or test compounds have been described above, and others are known in the art. Preferred mass spectrometric techniques are MALDI TOF MS and MALDI MS/MS, atmospheric pressure ionization techniques (API) such as electrospray ionization (ESI) MS, ESI-MS$^n$ and atmospheric pressure chemical ionization (APCI) MS and APCI MS$^n$; accordingly, in preferred embodiments, the mass spectrometer is capable of operating in single MS or multidimensional MS modes. A variety of commercially available mass spectrometers can be used as the mass spectrometer of the system.

In preferred embodiments, the system includes additional components. For example, the sample handler preferably transfers samples from the capillary array to an automated sample clean-up and preparation station. For example, robotic workstations can provide sample clean-up by filtration, precipitation, solid-phase extraction, or other known techniques for removing extraneous materials and contaminants and/or concentrating the sample prior to analysis.

Another preferred component of the systems of the invention is an automated station for performing biomarker purification or separation. In one embodiment, gel electrophoresis (preferably 2D electrophoresis or capillary gel electrophoresis) is use for biomarker (e.g., protein) purification. Commercially available automated stations for performing capillary electrophoresis are available (e.g., the ProteomeLab PA 800 from Beckman Coulter, Inc.).

In certain embodiments, the system further includes an automated workstation for further processing of biomarkers after purification or separation. For example, digestion of proteins isolated from a gel electrophoresis separation is used to prepare a sample for MS analysis. As previously described, automated workstations for in-gel digestion, sample cleanup, and MALDI spotting are commercially available.

The components of the system are preferably controlled by a computer control and data collection system capable of tracking each sample from start (capillary microcosm) to finish (mass spectrometric analysis). The computer system can monitor the automated processes and collect data such as retention times (in chromatography or electrophoresis) and molecular weight of ions in the mass spectrometer. In preferred embodiments, the computer system further comprises a molecular weight fragment database for determining the structure of compounds, or the identity of peptide sequences, present in the samples. Such systems are readily available and can be selected according to the type of analyte to be determined.

FIG. 1 shows one embodiment of a system according to the invention. Collection device 100 includes a capillary array 110 of individual microcosms 112. Sample handler 120, a sample handling station (e.g., a liquid handling station), removes a portion or aliquot of material from microcosms 112, and optional clean-up station 130 performs a sample processing procedure, e.g., a filtration and concentration procedure on the samples to remove contaminants and concentrate the biomarker of interest, if present. Each sample is optionally subjected to biomarker purification (e.g., protein purification or separation by gel electrophoresis) at workstation 140, followed by optional biomarker processing for analysis (e.g., after gel electrophoresis of peptides or proteins, in-gel digestion, sample cleanup, and MALDI spotting) at workstation 150. Finally, prepared samples are analyzed in mass spectrometer 160 (which can be a MALDI mass spectrometer).

The operations are controlled and coordinated by computer 170, and the results of these operations (data) are stored in central database 180 for analysis, including comparison and matching of mass spectral data to databases, and/or sequencing of peptides from MS$^n$ peptide fragment data. It will be appreciated that a central computer as shown in FIG. 1 is convenient but not required for sample analysis; each individual workstation can optionally be controlled by an associated computer.

Methods of Diagnosing, Screening and Optimizing Therapeutic Regimens

Another application of the devices and methods of the invention is in the study or optimization of treatment regimes. It is generally recognized that different patients can react in differing ways to standardized therapies (see, e.g., Mancinelli L, Cronin M, Sadee W., *AAPS Pharm Sci.* (2000) 2(1):E4). For example, genetic differences in liver enzyme profiles can result widely-differing rates of metabolism of drugs, resulting in a patient receiving a dose that may be either so large as to be harmful or so small as to be ineffective. According to the invention, a variety of therapeutic conditions can be screened in situ, without exposing the patient to any potentially dangerous conditions. Thus, the invention provides personalized, improved methods for optimizing therapy and improving patient safety and quality of life.

In one embodiment, the invention provides a method for screening treatment conditions without exposing a patient to potential harmful conditions. In one embodiment, the method includes a) providing a device comprising a housing and an array of test chambers, each of the test chambers being in fluid communication with a fluid manifold, and each of the test chambers containing either i) test cells or ii) control; b) exposing at least one of the test chambers to a test fluid and a candidate pharmaceutical agent; c) determining the effect of the candidate pharmaceutical agent on the test cells; and d) selecting an optimized medical treatment for the patient. In certain embodiments, the method comprises exposing test cells in a capillary array to a plurality of treatment conditions, and determining the effect of the treatment conditions on the cells.

In this embodiment, the capillary chambers of the device will typically be charged or loaded with a test sample, e.g., a tissue sample or cell culture of normal or abnormal cells (or both), a sample of disease-causing bacteria, or the like. For example, to treat a patient afflicted with cancer, a biopsy of the cancer can be taken by any conventional method (e.g., needle biopsy), and a sample of the cancerous cells placed in one or more capillary chambers of the ISMA device. In certain embodiments, a sample of one or more normal cell samples or cultures (e.g., epithelial cells, which are known to be sensitive to many conventional chemotherapeutic agents), either from the patient or a normal control, will also be present in one or more of the capillary chambers. The microcosm chambers can be provided with any media required for maintaining the viability of the tissue sample, such as growth media, growth factors, and the like.

When the chambers have been prepared with test samples, the device can then be contacted with or immersed in a test fluid, such as a biological fluid (such as whole blood, serum, or plasma) drawn from the patient. Alternatively, the device can be connected to a fluid conduit, such as an intravenous line or a catheter, to provide a bodily fluid to the device (which is located ex vivo). In still another embodiment, the device is implanted in the patient's body and is in contact with a biological fluid in situ. In embodiments in which blood is used as the test fluid, the device of the invention preferably is constructed so that blood-contacting surfaces are made of, or coated with, materials that do not cause blood coagulation. Anti-coagulant materials are known in the art, and include heparin and other compounds.

In certain embodiments, the device can be configured to be wearable on or adjacent to a body surface, e.g., by the patient. In this embodiment, a flexible housing can be used to permit the device to conform to the body of the wearer. The device can be insulated and/or heated to maintain a temperature similar to the body temperature of the wearer, in order to maintain an environment for tissue samples closely simulating the in vivo environment.

The effect of different treatment (e.g., chemotherapeutic) regimes (e.g., different agents, time courses, or concentrations of chemotherapeutic agents) can then be assayed by adding the appropriate agents to the test fluid or fluid stream and observing any effects on the sample cells. The amount of therapeutic agent, the duration of treatment, or the combination of different therapeutic agents can be assessed in a single ISMA by directing fluid to the appropriate chambers as the therapeutic compounds are added to the fluid. Alternatively, the chemotherapeutic agents can be provided in the capillary chambers together with the cell samples, and the effects on the cells in each capillary chamber can be observed independently.

As an example, the effects of chemotherapy on a normal cell culture can be compared to the effects of the same therapy on a cancer cell biopsy sample, to determine whether acceptable anti-cancer effects can be observed on cancer cells while sparing normal cells. The comparison can be performed, e.g., by removing the cells from the device and assessing cell viability for normal and cancerous cells, by any of a variety of well-known methods. Cells can be assessed to determine, e.g., growth rates, cell cycle progression, expression of gene products related to programmed cell death, and the like. In certain embodiments, proteomic analysis of cells from the microcosms (e.g., normal or cancer cells after treatment in one or more microcosms with a potential therapeutic agent) can be performed using MS-based analysis systems as described above, e.g., to determine levels of protein expression in normal and cancerous cells before and after treatment to determine which proteins are affected by the treatment.

In another embodiment, the invention provides a method for optimizing medical treatment for a patient, in which the method includes the steps of a) providing a device comprising a housing and an array of test chambers, each of the test chambers being in fluid communication with a fluid manifold, and each of the test chambers containing either i) a candidate pharmaceutical agent or ii) a control; b) exposing each of the test chambers to a biological fluid of the patient; c) determining the effect of the candidate pharmaceutical agent on the biological fluid; and d) selecting an optimized medical treatment for the patient.

It will be appreciated by the skilled artisan that in certain embodiments, the device of the invention can be used to determine the effects of potential treatment regimens without exposing the patient to the treatment itself. Because the test compounds and effluent from the test chambers can be collected and retained within the housing, the patient is never exposed to any potentially harmful materials. This feature of the invention permits the collection of data on human or animal response to chemicals, materials or conditions that cannot easily be studied by conventional means (e.g., for ethical reasons).

For example, potential drugs contained within the test chambers of the device can be exposed to a biological fluid of the patient, such as blood, which is admitted into the fluid manifold of the device. Each chamber can contain, e.g., a control (such as an inert polymer matrix, or a sample of normal tissue or cells) or a candidate pharmaceutical agent or mixture of agents. In chambers containing a candidate pharmaceutical agent, following exposure of the biological fluid to the candidate agents in the test chambers, the effect of the potential treatments can be determined. As described above, the devices and methods of the invention provide a convenient and ethically-acceptable means for performing research on human or animal interactions with any type of material or life form.

In certain embodiments, the candidate pharmaceutical agent comprises, e.g., an antibiotic, an antineoplastic agent, an antidiabetic agent, an anticoagulant agent, an anti-inflammatory agent, a vaccine, an anti-angiogenic agent, or a natural or synthetic nucleotide, polynucleotide or polynucleotide mimetic (such as DNA, RNA, or peptide nucleic acid (PNA)). In certain embodiments, the biological fluid is blood. In certain embodiments, the device can be miniaturized and adapted for implantation into the patient's body, while in other embodiments, the device can be adapted for connection to a fluid conduit such as an intravenous line or catheter.

In certain embodiments, the step of determining the effect of the candidate pharmaceutical agent on the biological fluid comprises determining the bioavailability, biodistribution, biostability or metabolism of the candidate pharmaceutical agent in the biological fluid. For example, after exposure of blood to a candidate pharmaceutical agent in the device, the concentration of the drug can be determined, either through sensors embedded in the device, or by removing samples from the test chambers for laboratory testing. The concentration of drug in blood cells, e.g., white blood cells, or the amount of drug bound to circulating protein, can be determined by separating these components from whole blood and measuring drug concentrations. Similarly, the ability of a candidate drug to penetrate cell layers (e.g., in a tissue biopsy sample) can be readily determined using the devices and methods described herein. Such determinations can be used to predict whether a treatment will be effective when the drug is dosed to the patient, without the need for actually administering the drug to the patient. Different amounts of drug, formulations of drug (e.g., extended release formulations), and other parameters can be similar tested in a rapid and safe fashion.

In certain embodiments, the step of determining the effect of a candidate pharmaceutical agent on the biological fluid (or test cells) comprises determining the antibiotic effect of a candidate pharmaceutical agent on a blood-borne pathogen. For example, in certain embodiments, at least some of the test chambers can include filters and/or growth media for culturing microorganisms. For example, if the candidate suffers from an infection, the device can be used to determine the type and strain of the microorganism responsible for the infection in much the same way that other environmental microorganisms can be studied with the devices of the present invention, as described above. Still other test chambers can include both a filter and/or growth medium for culturing microorganisms and an agent for treating a disease condition caused by the microorganism, for example, an antibiotic. The invention thus provides methods for simultaneously determining which microorganisms are present in a biological fluid, and which treatments are likely to be effective in treating the infection.

In a related embodiment, the invention provides devices and methods for determining whether a subject suffers from parasitic infection, and optionally for determining an effective treatment for such parasitic infection. Exemplary parasites include *Schistosoma mansoni, Plasmodium falciparum, Plasmodium vivax, Plasmodium ovale, Plasmodium malaria, Leishmania donovani, Treponema pallidus*, and the like. These parasites can be trapped or captured by placement of a device of the invention in a biological fluid (such as blood, urine, or feces) and test compounds present in certain of the chambers of the capillary array (or added from reagent reservoirs) can be screened to determine an effective compound and dosage level.

In another embodiment, the step of determining the effect of the candidate pharmaceutical agent on the biological fluid comprises determining the ability of a candidate pharmaceutical agent to stimulate production of cell signals such as cytokines, hormones, nitric oxide, and other intercellular or intracellular signaling molecules.

Example 1

One embodiment of the present invention takes the form of an in situ microcosm array (ISMA) sampler or testing device 1. This embodiment of the device is well-suited for analysis of environments such as sub-surface water sources or aquifers. As shown in FIGS. 1-4, its principal components include: a housing or container 10 having a fluid inlet 12 and outlet 14, a plurality of capillary microcosms 16 situated within this housing, with these capillaries 16 making up what is referred to as a microcosm array, each of these capillaries 16 having an inlet 18 and outlet 20 that are configured so as to allow for fluid flow through the capillaries 16, each of these capillaries contains an optional filtration material 22 that is selected for its ability to foster microorganism collection in the individual capillaries, upper 24 and lower 26 valve plates having openings 28 that are configured to be alignable with the capillary inlets 18 and outlets 20, a pneumatic cylinder 30 with coupling means 32 and an assortment of springs 34 serves to enable these valves to be moved laterally so as to open or close the capillaries' inlets 18 and outlets 20, gasketing pads 36, 38 serve to prevent leakage from these openings, a pump 40 is connected to the container's inlet 14 and is sized so that it can draw fluid from the environment surrounding the container 16 and push it through the container's inlet 12 and through the capillaries 16, a collecting device or a bladder 42 is connected to the pump's outlet and is used to collect the flow through the container 16, a check valve 44 connected between the pump 40 and bladder 42 prevents backflow of fluid through the container 16, a weight 46 serves to provide ballast for suspending via an umbilical cable 48 the sampler 1 down a suitably drilled well that extends into a region of interest.

In this Example, the dimensions of the device were based on commercially available 96-position (8 wells by 12 wells) microtiter plate format (e.g., Wheaton Scientific Products); similar 384, 1536 (or more) plate formats can also be used. Each well or "microenvironment" of the device consisted of a Teflon block with 96 drill holes representing individual microcosm capillaries (1.12 mL; 0.295 inch in diameter by 1 inch in length).

The inclusion into the ISMA sampler 1 of a pump 40, closure mechanism valve plates 24, 26, and semi-permeable membranes allows one to first inoculate and then incubate the device in the environment without removing (and potentially harming) the resident microbes from their natural environment. Pump configurations other than those shown in the drawings include, but are not limited to, multi-channel pumps and pump arrays that deliver fluids to the inlet of one or more individual microcosm capillaries.

The ISMA sampler 1 of the present invention can be equipped with a collecting device or a bladder 42, which in this Example is located outside the housing 10 for the capillary array. Fluid flowing through the array exits the container through a fluid-tight connection and is collected in the bladder. Displacement of air from the collection device may be desirable, and can be achieved by inclusion in the collection device of a bleed valve allowing air to escape via a piece of tubing rising along the umbilical cable to a location some distance above the fluid intake.

As the fluid from the environment flows through the device, microorganisms and chemicals can be trapped in the capillary microcosms 16. When the collection device is full, a float or other fluid sensor can trip power to the pump and actuate the valve plates 24, 26 of the closure mechanism, thereby sealing the array. Immediately, or after an additional incubation period in batch mode, the device 1 can be removed from the environment for further analysis.

Example 2

In this Example, cells of a bacterium (*S. wittichii* strain RW1) were identified using MALDI TOF mass spectrometry and multidimensional mass spectrometry in conjunction with peptide mass fingerprinting and peptide sequencing.

Culturing of Strain RW1.

Liquid cultures of *S. wittichii* strain RW1 (DSMZ 6014) were grown at 30° C. in a water bath shaker in M9 phosphate-buffered minimal medium supplemented with (i) dibenzofuran (DF) crystals (Sigma-Aldrich; Milwaukee, Wis.), (ii) 50 mM glucose, or (iii) both. Saturated DF medium contained approximately 3-5 mg $l^{-1}$ of the binuclear aromatic compound in the dissolved phase. Turbidity of the cultures was monitored using a DR/4000U spectrophotometer (Hach, Loveland, Colo.) at a wavelength of 560 nm. Viable bacteria were enumerated by plate counts using M9 medium supplemented with 1.5% agar (Difco, Franklin Lakes, N.J.) and 5 mM sodium benzoate. Negative control samples composed of cells of RW1 lacking the dioxin dioxygenase were obtained via growth of the bacterium on non-selective Luria Bertani broth, a complex medium that represses dioxygenase expression.

Microorganisms Serving as Negative Controls.

More than 20 different Proteobacteria served as negative controls throughout this study. Most of these represented poorly characterized environmental monocultures and mixed cultures that had been obtained via selective enrichment using dioxin-like compounds as sole sources of carbon and energy. *Pseudomonas putida* KT2440 (DSMZ 6125) was the only negative control strain for which the complete genome was available in searchable online databases. All cultures were grown in selective conditions on aromatic substrates to maximize the expression of aromatic-ring dioxygenases.

Sample Preparation.

Four different types of cell preparations were furnished for MALDI-TOF MS. Cells growing in the early, mid and late exponential phase were harvested by centrifugation (3,000× g, 30 minutes, 4° C.), washed, and resuspended in 50 mM $NH_4HCO_3$ (Fraction 1; undisrupted cells). Biomass was disrupted on ice using a Sonic Dismembrator (Fisher Scientific, Pittsburgh, Pa.) on low setting for three bursts of 10 s, with cooling periods of 30 s between bursts, yielding Fraction 2 (disrupted cells). Sonicated cell suspensions were centrifuged (13,500×g, 5 minutes, 4° C.) to separate the supernatant of the crude cell extract (Fraction 3; whole cell extract) from the pellet (Fraction 4) consisting primarily of cell debris and undisrupted whole cells. For experiments involving 2-dimensional gel electrophoresis, whole cell extracts were divided into two equal volumes (sample splits) to allow for additional analysis by MALDI-TOF MS; reported CFU in the sample are corrected for the loss of biomass resulting from splitting of the samples.

In Silico Digestion.

Peptides resulting from tryptic digestion of the alpha- and beta-subunits of the dioxin dioxygenase were predicted from sequences deposited in the NCBI database (http://www.ncbi.nih.gov/) using MS-Digest (http://prospector.ucsf.edu/). Screening of combinations of various search parameter settings resulted in the following optimal settings: the in silico digests were performed using trypsin and disallowing missed cleavages or post-translational modifications. Cysteines were presumed to be unmodified; as were the N- and C-termini of the peptides. The mass range was specified as 500-5,000 Da; multiply charged ions were not considered.

MALDI-TOF MS Analysis.

Samples (25 ul) were digested with 200 ng trypsin in 50 mM $NH_4HCO_3$ at 37° C. overnight, vacuum-dried in a Savant SVC100 SpeedVac (GMI, Albertville, Minn.), desalted using $C_{18}$ Omix microextraction column tips (Varian, Palo Alto, Calif.) and mixed with matrix solution (~1.5 ul) consisting of 10 mg $ml^{-1}$ of alpha-cyano-4-hydroxy-cinnamic acid (CHCA) in 50% acetonitrile and 0.1% trifluoroacetic acid (TFA). A stainless steel 96-well MALDI target plate (Applied Biosystems, Foster City, Calif.) was spotted with approximately 1 ul of the sample/matrix solution, which was then air-dried. Spectra were acquired using a Voyager DE-STR MALDI-TOF MS (Applied Biosystems, Foster City, Calif.) in positive reflector mode (m/z 500-5000; 50 laser shots per spectrum). Initial external calibration was performed using a standard peptide mixture (human brakykinin fragment 1-7, 757.3997 Da; human adrenocorticotropic hormone fragment 18-39, 2465.1989 Da; bovine insulin chain B, oxidized, 3494.6513 Da) purchased from Sigma (St. Louis, Mo.). Additional internal calibration was carried out as described below.

Mass Spectral Data Analysis.

Mass spectral data were analyzed and manipulated using Data Explorer software (Applied Biosystems, Foster City, Calif.). Spectra were deisotoped using the manufacturer's settings. Internal calibration was carried out using trypsin autolysis peaks. Acquired data were analyzed by comparison to in silico information contained in the NCBI databases (http://www.ncbi.nih.gov) using PMF. The 300 most intense peaks were searched against the NCBI taxonomy subset "All Bacteria" (753,000+ sequences) at a mass tolerance of 50-100 ppm using MASCOT. Additional search parameters included disallowing for missed cleavages and either fixed or variable post-translational modifications. Probability scores for positive identification were determined using the statistical algorithm in the program described elsewhere for peptide-mass fingerprinting (PMF) (Pappin, D. J. C., P. Hojrup, and A. J. Bleasby, Curr. Biol. 3:327-332 (1993).

Peptide Sequencing.

Protein identifications obtained by PMF were confirmed in selected samples via sequencing of the target mass at m/z 3036.3 using an ion trap mass spectrometer (LCQ Deca XP; Thermo Electron Corporation, MA) in conjunction with an atmospheric pressure MALDI source (Mass Tech Inc., MD). Presence of the alpha-subunit of the dioxin dioxygenase was confirmed by submission of detected fragment ions to the Sequest database.

Results

In Silico Analyses.

Theoretical (in silico) digestions were performed to construct peptide maps of the large (alpha-) and small (beta-) subunits of the dioxin dioxygenase. The porcine protease used in this study, trypsin (E.C.3.4.21.4), cleaves proteins after the amino acids lysine and arginine, unless these are followed by a proline. Digestion yielded individual amino acids and peptides, the latter ranging in length from 2-35 amino acids. For the alpha-subunit, there were 31 predicted potential MS targets in the experimentally defined detection range (mass-to-charge ratios of m/z 500-5,000), covering 94% of the amino acids of the total protein. The remaining 6% of the protein mass was composed of peptides situated outside of the detectable range (m/z<500). The beta-subunit was calculated to yield a maximum of 15 detectable tryptic peptides, suggesting a maximum theoretical protein coverage of 84% (data not shown).

Screening of Various Fractions of RW1 Cells for the Dioxin Dioxygenase.

Initial experiments concentrated on the feasibility of detecting the dioxin dioxygenase in four different fractions of processed cell cultures (see FIG. 6). Proteins contained in the various cell fractions were digested, purified and desalted via passage through a pipet tip functioning as a $C_{18}$-microextraction column. Purified digests were mixed with matrix, and analyzed by PMF using MALDI-TOF MS as shown in the schematic (FIG. 6). Investigated cell fractions included undisrupted cells (Fraction 1), cells disrupted by sonication (Fraction 2), whole cell extracts representing the supernatant of disrupted, centrifuged cells (Fraction 3), and the corresponding pellet consisting of cell debris and residual whole cells (Fraction 4). Since the optimal amount of biomass for the assay was not known a priori, experiments were performed using a range of initial cell quantities ($10^5$-$10^8$ cells).

Fraction 1.

Analysis by peptide mass fingerprinting of a digest of $10^8$ undisrupted cells of RW1 yielded ten target peaks above the baseline noise: m/z 685.4, 951.5, 1,234.6, 1,393.7, 1,541.8, 1,847.8, 2,005.0, 2,194.0, 2,222.1, and 3,036.3. A list of 300 ions having the greatest signal intensities was generated and submitted to online protein databases representing the kingdom of Bacteria. The data query returned the alpha-subunit of the dioxin dioxygenase as the best fit among 753,000+proteins. The resultant Mascot score of 52 indicated that the search result was not statistically significant (p>0.1), however. Overall, the 10 target peptides provided 31% protein coverage.

Fraction 2.

Analysis of a digest of $10^7$ disrupted cells of RW1 resulted in detection of nine target peptides of the alpha-subunit of the dioxin dioxygenase. Compared to Fraction 1, the mass at m/z 951.5 was missing and an increase in the level of noise was observed in the range from m/z 1,000-3,200. Again, database searching returned the alpha-subunit of the dioxin dioxygenase as the best match, with a statistically significant (p<0.05) Mascot score of 69. Protein coverage was 32%.

Fraction 3.

Analysis of supernatant obtained by centrifugation of $10^7$ disrupted cells of RW1 yielded the best result. The mass spectrum had a very low level of noise across the entire m/z range of interest. Major detectable ions were clustered between m/z 500 and 3,200. In the spectrum shown, four of the eight most intense peaks-detected at m/z 1,393.7 (100% relative intensity), 586.3 (22%), 2,222.1 (17%), and 962.5 (15%)—matched in silico values calculated for peptides of the alpha-subunit of the dioxin dioxygenase; the second intense ion at m/z 842.5 corresponded to a trypsin autolysis product that was used as an internal standard for mass calibration. A total of 13 target peaks were detected, resulting in confident protein identification (p<0.00001) by Mascot searching, with a score of 105 and a protein coverage of 34%. Target ions detected at lesser intensities included m/z 685.4 (13% relative intensity), 919.4 (7%), 951.5 (13%), 1,234.6 (9%), 1,541.8 (8%), 2,005.0 (10%), 2,194.0 (11%) and 3,036.3 (4%). The ease of detection of the alpha-subunit in whole cell extract is consistent with previous reports that localized dioxin dioxygenase activity to the soluble proteome of extracts from cells grown on DF.

Fraction 4.

Analysis of digested pellets obtained by centrifugation of disrupted cells yielded noisy mass spectra that did not show any target m/z regardless of the amount of biomass processed. This finding was consistent with literature indicating cell pellets to be depleted in dioxin dioxygenase activity relative to whole cell extracts of RW1 (Fraction 3). Overall, the results demonstrated that the dioxin dioxygenase is most easily detectable by PMF in digested whole cell extract. Therefore, the sensitivity of PMF analysis was further investigated in the latter matrix.

Sensitivity Analyses and Robustness of the Assay.

To determine the biomass range suitable for positive identification of Strain RW1 via PMF of the alpha-subunit of the dioxin dioxygenase, whole cell extracts of $10^5$-$10^{10}$ DF-grown CFU were analyzed following digestion with a standard amount of 200 ng of trypsin. Positive protein identification with significant probability-based Mascot scores of >68 (p<0.05) were obtained consistently when >$10^6$ cells were processed and analyzed. Analysis of extracts obtained from $10^7$ and $10^8$ DF-grown cells yielded Mascot scores ranging from 73 to 105 (p<0.01-0.00001) and 84 to 111 (p<0.001-0.00001), respectively; in these experiments, the number of matched peptide masses ranged from 10 to 13 and 12 to 14, respectively, with protein coverages for the alpha-subunit of the dioxin dioxygenase ranging from 31-34% ($10^7$ CFU) and from 37-43% ($10^8$ CFU). Analysis of ≤$10^6$ CFU yielded no target ions and no significant matches for either the two target proteins or any of the more than 753,000 proteins contained in the non-redundant NCBI database at the time of data analysis. Similarly, no database matches were found in experiments using ≥$10^9$ CFU. A total of 15 different peptide masses, corresponding to the alpha-subunit of the dioxin dioxygenase, were detected in more than 100 experiments conducted with biomass harvested in the early, mid and late exponential growth phase (total protein coverage of 45%). In contrast, none of these target peptides were found and no positive identifications of the dioxin dioxygenase were obtained during analysis of the more than 20 negative control strains that represented a broad spectrum of microorganisms capable of catabolizing dioxin-related aromatic compounds.

Results of repeatedly performed experiments were very consistent. The following variables had no detectable effect on the outcome of the experiment (data not shown): substituting alpha-cyano-4-hydroxy-cinnamic acid (CHCA) for 3,5-dihydroxybenzoic acid (DHB) as the ionization matrix, type of $C_{18}$-microextraction column used (n=2), and identity of the operator (n=3). However, when cells were harvested late into the exponential growth phase (deceleration phase), a slight drop in Mascot scores was observed.

Interestingly, the beta-subunit of the dioxin dioxygenase was never identified by database searching in any of these experiments. This is surprising because the observed removal of DF during growth of RW1 cultures indicated the presence of this essential protein at quantities equimolar to those of the alpha-subunit. Although some target ions of the beta-subunit were present, as determined by manual identification, the signal intensities of these peptide masses at m/z 563.4 (1% relative intensity), 607.3 (2%), 693.3 (4%), 832.5 (8%), 848.5 (10%), 1,077.6 (6%) typically were at or near the baseline noise level. Following spectral processing and data reduction using a peak threshold of approximately 5-10% relative intensity, these ions mostly were rejected and did not enter into the online database query; this effectively prevented a potential identification of the beta-subunit when using the online search algorithm.

Effect of Growth Substrate on Strain Identification.

Cultures of RW1, grown in phosphate-buffered mineral salt solution supplemented with the growth substrates (A) DF, (B) DF plus glucose, and (C) glucose only, were processed and analyzed by MALDI-TOF MS and 2D gel electrophoresis. The alpha-subunit of the dioxin dioxygenase—i.e., the previously established biomarker of dioxin degradation-enabled cells of RW1—was identified readily in the digested soluble proteome of DF-grown cells, with scores as high as 111, indicating a very low probability of false-positive misidentification (p<0.00001). Detection of up to 14 target peptides in whole cell extracts of $10^8$ CFU resulted in a protein coverage of 43%, the best result achieved. Again, the ions corresponding to peptides of the alpha-subunit were among the most prominent in the mass spectra.

The alpha-subunit of the dioxin dioxygenase also was returned as the best database match when analyzing glucose-grown cells of RW1 that were co-exposed to DF for enhanced expression of the dioxin dioxygenase; however, the corresponding score was not significant (p>0.05), necessitating peptide sequencing for unambiguous protein identification. Compared to DF-grown cells, the signal intensity of target peaks was lower in glucose-grown biomass co-exposed to DF. No target peaks were detected when analyzing biomass grown on glucose in the absence of DF, and no significant matches were found for any of the 753,000+proteins contained in the non-redundant NCBI database. Analysis of cells grown using non-selective complex media, e.g., Luria Bertani broth, also revealed no ions of interest in the mass spectra recorded. Lack of detection of the alpha-subunit in LB-grown cells was consistent with literature information indicating repressed dioxin dioxygenase expression during growth of RW1 on complex media.

The present study employed PMF on minimally processed microbial cells. Experimental results of the present study revealed the value and power of this non-traditional usage of PMF by MALDI-TOF MS for the identification and phenotypic characterization of certain environmental microorganisms such as Strain RW1.

In contrast to mass spectral microbial fingerprinting, PMF is more powerful because specific target proteins can be selected a priori and their corresponding ions (peptide masses) can be predicted in silico. Identification is based on the detection of multiple fragments of a given protein rather than on a single molecular ion. Therefore, protein matches by PMF have a quantifiable confidence level and often are statistically highly significant even when searching non-restricted, complex databases containing hundreds of thousands of proteins. The identity of detected proteins can be ascertained without having to obtain and analyze authentic protein standards, an important advantage when attempting to identify environmental isolates whose proteins have never been purified. Since the function of the detected biomarker either is known or can be inferred, PMF of microbial cells can reveal critical information on biomass physiology that otherwise would be difficult or impossible to obtain.

The analysis strategy and methodology presented in this Example is attractive for application, e.g., in the field of bioremediation for several reasons. One advantage of this assay is its ability to identify cells of RW1 and simultaneously yield information on their most critical phenotypic characteristic that drives the removal of dioxins from contaminated environments during bioaugmentation: the expression of appreciable quantities of the dioxin dioxygenase. Analysis of whole cell extracts by PMF can inform on the extent to which vegetative cells of RW1 are charged with this enzyme. Since the assay is performed on a non-purified bacterial proteome fraction, only cells containing appreciable quantities of the dioxin dioxygenase are detectable by PMF.

The methodology demonstrated here for a dioxin-degrading bacterium may be extended to other microorganisms containing large quantities of characteristic proteins. Enzymes expressed at moderate quantities also may be suitable targets as long as their corresponding peptides ionize favorably, similar to those of the alpha-subunit of the dioxin dioxygenase. Since the technique is inexpensive and potentially may be automated, it could prove valuable in bioremediation and other areas of applied and environmental microbiology.

Additional benefits of the assay are its reproducibility, robustness and the potential for unattended high-throughput analysis during routine screening of environmental isolates.

Example 3

In this Example, a parasite is detected by use of MALDI TOF MS.

Schistosomes are parasites in a wide variety of warm-blooded hosts. In mammals and humans, they cause serious diseases. It is estimated that hundreds of millions of people worldwide are infected with schistosomes. Infection occurs when cercaria, a free-swimming larval form of the parasite found in contaminated water, penetrate the skin of the mammalian host.

Figure 7:
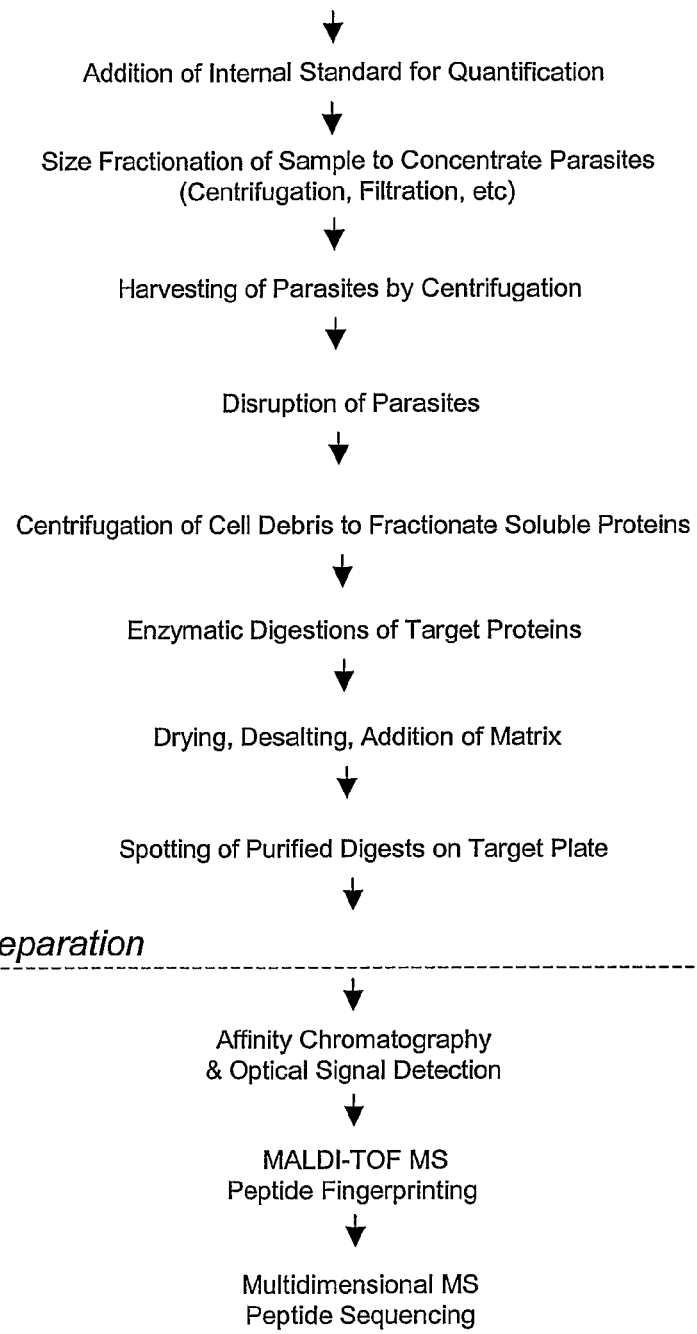
FIG. 7 is a scheme showing a method for identifying biological cells, including parasites.

Detection of the cercariae in water is conventionally performed by skimming the cercariae from the surface of the water, followed by visual observation by a parasitologist. As an alternative, use of MALDI TOF MS was investigated. A schematic representation of the detection method is shown in FIG. 7 (some optional steps are also shown in FIG. 7).

Methods.

Lyophilized cercariae of *Schistosoma mansoni* were divided into fractions of approximately 2,500 cercariae and resuspended in 50 mM ammonium bicarbonate. Cells were disrupted using a Fisher 550 Sonic Dismembrator (Fisher Scientific) and spun at high speed (13,500 g, 5 minutes, 4° C. in a Beckman Microfuge 18) to remove cell debris. The supernatant was assayed colorimetrically for protein content using the bicinchoninic acid assay (Pierce, Rockford, Ill.).

Samples containing 400 ug protein were digested with 200 ng proteomics grade trypsin (Sigma, St. Louis, Mo.) in 50 mM ammonium bicarbonate buffer at 37° C. for 18 hours, then vacuum dried and desalted using $C_{18}$ Omix microextraction column tips (Varian, Palo Alto, Calif.) and mixed with matrix solution (alpha-cyano-4-hydroxy-cinnamic acid (CHCA) in 50% acetonitrile and 0.1% trifluoroacetic acid (TFA)) prior to deposition in a 96-well MALDI target plate (Applied Biosystems, Foster City, Calif.). Spectra were acquired using a Voyager DE-STR MALDI-TOF MS (Applied Biosystems, Foster City, Calif.) in positive reflector mode (m/z 500-5000; 50 laser shots per spectrum).

Mass spectral data were analyzed and manipulated using Data Explorer software (Applied Biosystems, Foster City, Calif.). Spectra were deisotoped and an internal calibration was carried out using trypsin autolysis peaks. Mass lists were generated and compared to theoretical peptides using the NCBI databases and MASCOT.

Results.

Peptide fingerprinting analysis of supernatant from disrupted cells of cercariae using MALDI-TOF MS and searching of the NCBI metazoan database yielded stathmin-like protein gi|3641363 of *S. mansoni* as the best match among over 170,000 sequences searched.

These results show that infectious schistosome cercariae can be detected successfully using MALDI-TOF MS of minimally-processed crude cell extracts. This novel detection technique shows that automated high-throughput analysis of environmental schistosome parasites is feasible. The method has sufficient discriminatory power to distinguish between schistosomes which infect birds and those which infect humans. This method can be used to detect schistosomes in the environment or in clinical specimens by both one-dimensional and multidimensional mass spectrometry.

Example 4

In this Example, a bacterial protein was identified from a complex mixture.

For this Example, a sample mixture was prepared. Samples contained the target organism (*Sphingomonas wittichii* RW1) and four other bacteria (*E. coli, Pseudomonas putida* KT2440*, Enterococcus* sp. and *Burkholderia xenovorans* LB400). The samples were diluted to 1:1 and 100:1 (target: interfering bacteria) and soluble fractions were digested with trypsin overnight. Known peptides from the target (dioxin dioxygenase) were selected for blind sequencing, and the highest intensity peaks were subjected to MS/MS and $MS^n$ (i.e., multiple-dimension MS, such as MS/MS/MS). Data were analyzed using a Kratos Axima QIT and searched against the NCBInr database using Mascot (www.matrixscience.com).

It was found that the target bacterium (*Sphingomonas wittichii* RW1) was not detected from a mixture of equal amounts of each bacterial type. However, the target bacterial species was successfully identified with confidence (p=0.00075) from a mixture in which the target represented the predominant bacterial species (100:1:1:1:1 mixture of bacteria types). Also detectable was the dioxygenase gi|37727200 of *Pseudomonas putida* KT2440.

Example 5

This Example demonstrates the identification of viral protein from a complex stool matrix.

For this Example, a sample list was created using varying concentrations of recombinant Norovirus virus-like particles (VLPs) and virus-free stool extracts. Pure VLP stock was used to determine the detection limit of the virus in the MALDI-QIT-TOF. Samples were analyzed by MS, MS/MS and $MS^3$ by selectively targeting the viral peptides. The VLPs were challenged against increasingly concentrated stool matrices, ultimately to a 1× stool concentration. Data were analyzed using a Kratos Axima QIT and searched against the NCBInr database using Mascot (www.matrixscience.com).

It was found that the target viral particles could be detected with a detection limit of 10 femtomoles of purified virus particles.

The contents of all patents, patent applications, and publications cited herein are hereby incorporated by reference in their entirety.

Other embodiments are within the following claims.

What is claimed is:

1. A method for characterizing cells in an environment, the method comprising:

a) placing a collecting device in the environment to collect microorganisms, the collecting device comprising:
   i) an array of capillary microcosms for trapping cells, wherein fluid flow can be controlled through the capillary microcosms individually; and
   ii) a housing surrounding the array and having an opening to controllably permit cells from the environment to access the array;
b) retrieving the collecting device from the environment;
c) sampling at least one of the capillary microcosms to obtain at least one sample;
d) analyzing the at least one sample to characterize the cells in the environment.

2. The method of claim 1, wherein the step of sampling comprises using an automated sample handling device.

3. The method of claim 2, wherein the step of sampling at least one of the microcosms comprises:

a) obtaining the at least one sample using an automated sample handling device; and
b) concentrating the at least one sample for analysis.

4. The method of claim 3, wherein the step of analyzing comprises analysis by mass spectrometry.

5. The method of claim 4, wherein the mass spectrometry is MALDI TOF.

6. The method of claim 5, wherein the cells are characterized as whole cells.

7. The method of claim 5, wherein the step of analyzing further comprises preparing a cell lysate and analyzing said cell lysate.

8. The method of claim 4, wherein the step of analyzing further comprises comparing at least one molecular weight determined by mass spectrometry to a computerized library of molecular weights.

9. The method of claim 5, wherein the cells comprise a microorganism useful for bioremediation.

10. The method of claim 5, wherein the cell comprises *Sphingomonas wittichii* Strain RW1.

11. The method of claim 4, wherein the step of analyzing by mass spectrometry comprises analyzing an isotopically labeled molecule.

12. The method of claim 4, wherein the step of analyzing comprises determining a turnover rate of a compound of interest.

13. The method of claim 1, wherein each capillary microcosm comprises a fluid inlet, a fluid outlet, and a capillary chamber.

* * * * *